United States Patent [19]

Enomoto et al.

[11] 4,008,283

[45] Feb. 15, 1977

[54] 1,1-BIS(1-METHYL-2-VINYL-4,6-HEPTADIENOXY) ALKANE AND METHOD FOR THE PRODUCTION THEREOF

[75] Inventors: Satoru Enomoto, Fujisawa; Yutaka Mukaida, Tokyo; Mikiro Yanaka, Matsudo; Sadao Nishita, Tokyo; Hisayuki Wada, Tokyo; Hitoshi Takita, Tokyo, all of Japan

[73] Assignee: Kureha Kagaku Kogyo Kabushiki Kaisha, Tokyo, Japan

[22] Filed: June 17, 1976

[21] Appl. No.: 696,929

[30] Foreign Application Priority Data

Aug. 5, 1975 Japan .............................. 50-094690

[52] U.S. Cl. ........................... 260/615 A; 106/310; 106/311; 252/182; 252/364; 260/347.8; 260/611 A

[51] Int. Cl.$^2$ ........................................ C07C 43/30

[58] Field of Search ................................ 260/615 A

[56] References Cited

UNITED STATES PATENTS

| | | | |
|---|---|---|---|
| 2,183,317 | 12/1939 | Anden et al. | 260/615 A |
| 2,668,862 | 2/1954 | Price | 260/615 A |
| 3,584,010 | 6/1971 | Marbet | 260/615 A |

OTHER PUBLICATIONS

Manyik et al. Tetrahedron Letters 3813–3816, 1970.

*Primary Examiner*—Howard T. Mars
*Attorney, Agent, or Firm*—Lane, Aitken, Dunner & Ziems

[57] ABSTRACT

1,1-bis(1'-methyl-2'-vinyl-4',6'-heptadienoxy)alkane is obtained by acetal formation of 1-methyl-2-vinyl-4,6-heptadienol with an aldehyde. The 1,1-bis(1'-methyl-2'-vinyl-4',6'-heptadienoxy) alkane is a novel curing compound.

4 Claims, 3 Drawing Figures

1,1-BIS(1-METHYL-2-VINYL-4,6-HEPTADIENOXY) ALKANE AND METHOD FOR THE PRODUCTION THEREOF

FIELD OF THE INVENTION

This invention relates to a novel cross-linked curing compound and to a method for the production thereof.

BACKGROUND OF THE INVENTION

A cross-linked curing compound, 1-methyl-2-vinyl-4,6-heptadienol, of the formula:

$$CH_2=CH-CH=CH-CH_2-CH-CH-OH$$
$$\qquad\qquad\qquad\qquad\qquad\quad |\qquad\;\;|$$
$$\qquad\qquad\qquad\qquad\qquad CH_2=CH\;\;CH_3$$

has been disclosed in the "Tetrahedron Letters," No. 43 pages 3813–3816 (1970, United Kingdom). This compound is obtained by the reaction of butadiene with an aldehyde in the presence of a palladium complex catalyst. Since this compound has a conjugated double bond and a vinyl substituent, it is highly reactive. Therefore, cross-linking occurs in the presence of a catalyst such as a metal salt of naphthenic acid, an organic peroxide or azobis-isobutylonitrile or a curing reaction under heating. Thus, it is claimed to be useful as a reactive diluent for oil-based paints or air-drying alkyd-resin paints. However, we have demonstrated experimentally that this compound, when used as a diluent for an alkyd-resin paint, exhibits volatility so high as to degrade the workability of the paint.

SUMMARY OF THE INVENTION

It is, therefore, an object of this invention to provide a cross-linked curing compound of low volatility but yet high reactivity and a method for its production.

This object and the other objects of the present invention will become apparent from the following description.

We made a study in search of a way for accomplishing the object described above and have discovered that the compound obtained by acetal formation of the 1-methyl-2-vinyl-4,6-heptadienol with an aldehyde satisfies the requirements for a curing compound.

According to this invention, therefore, there is provided 1,1-bis(1'-methyl-2'-vinyl-4',6'-heptadienoxy)alkane which is a novel curing compound. The present invention further provides a method for the production of 1,1-bis(1'-methyl-2'-vinyl-4',6'-heptadienoxy)alkane, which method includes acetal formation of 1-methyl-2-vinyl-4,6-heptadienol with an aldehyde.

DETAILED DESCRIPTION OF THE INVENTION

The 1,1-bis(1'-methyl-2'-vinyl-4',6'-heptadienoxy)alkane of the present invention, is a compound of the generic formula:

$$(CH_2=CH-CH=CH-CH_2-CH-CH-O)_2 CH\; R$$
$$\qquad\qquad\qquad\qquad\qquad\;\;\;|\qquad\;|$$
$$\qquad\qquad\qquad\qquad\qquad CH_2=CH\;\;CH_3$$

wherein, R denotes H or an alkyl group having 1–7 carbon atoms. This compound is produced by acetal formation of the 1-methyl-2-vinyl-4,6-heptadienol with an aldehyde of the generic formula, RCHO, R denotes H or an alkyl group having 1–7 carbon atoms. This acetal formation may be carried out by an ordinary method in the presence of a catalyst. Examples of the catalyst which can be used in this reaction include calcium chloride, sodium sulfate, magnesium sulfate, calcium sulfate, silica gel, a molecular sieve, hydrogen chloride gas, and paratoluenesulfonic acid. Theoretically, it suffices to use 1 mol of an aldehyde per 2 mols of 1-methyl-2-vinyl-4,6-heptadienol for the acetal formation. To ensure thorough consumption of 1-methyl-2-vinyl-4,6-heptadienol, however, it is preferable to use the aldehyde in an amount slightly in excess of the theoretical value. The reaction time and temperature usually depend upon the kind and amount of the particular catalyst used and also the particular aldehyde starting material involved in the reaction. Generally a range of 1 to 24 hours and 0° to 100° C, preferably 0° to 50° C, are suitable reaction conditions. The aldehydes satisfying the purpose of this invention include formaldehyde, acetaldehyde, butylaldehyde and octylaldehyde, for example. It is also possible to use aromatic aldehydes such as benzaldehyde, hydroxybenzaldehyde and tolylaldehyde, and heterocyclic aldehydes such as furfuralaldehyde in place of the aldehydes enumerated above.

The physical properties of some 1,1-bis(1'-methyl-2'-vinyl-4',6'-heptadienoxy)alkanes are:

1,1-bis(1'-methyl-2'-vinyl-4',6'-heptadienoxy)ethane

Figure 1:
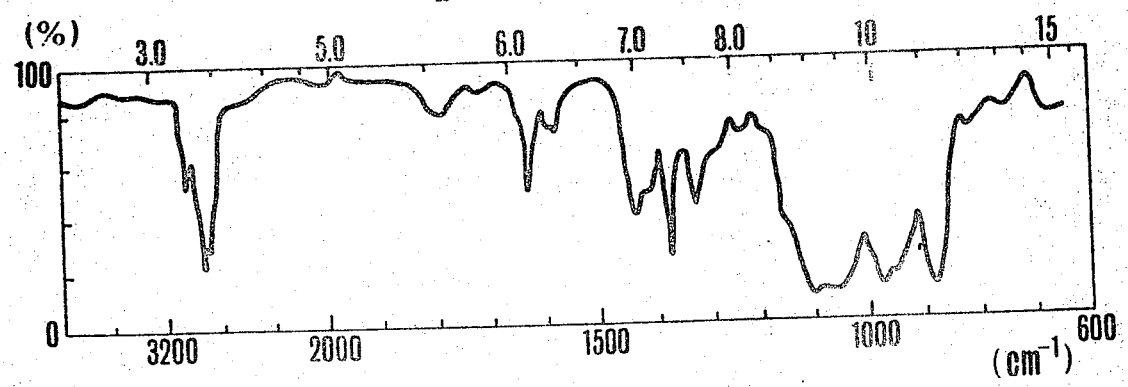
FIG. 1 represents an infrared absorption spectrum of 1,1-bis(1'-methyl-2'-vinyl-4',6'-heptadienoxy)ethane.

- Boiling point: 144° to 148° C/2mmHg (315°–320° C/760mmHg)
- Ultra violet absorption: λmax = 229 mμ
- Infrared absorption spectrum: as shown in FIG. 1
- Refractive index: $n_D^{25}$ = 1.4903
- Specific gravity: $d_4^{15}$ = 0.9025
- Viscosity: $\eta$ = 8.63 cst (centistokes) (25° C)
- Molecular weight: 349 (VPO method) (Theoretical value 380.5)
- NMR: Measurement values obtained from $CCl_4$ solution and tetramethylsilane
  δ($CCl_4$) ppm 0.95–1.30 (m) [ —CH₃ (9H) ]

1.93–2.50 (m) $\left[ =C-CH_2, =C-\overset{H}{\underset{|}{C}}-\;(6H) \right]$ 3.16–3.83 (m) $\left[ O-\overset{H}{\underset{|}{C}}-\;(2H) \right]$ 4.50–4.75 (m) $\left[ O-\overset{H}{\underset{|}{C}}-O\;(1H) \right]$ 4.75–5.28 (m) [ =CH₂ (8H) ]

5.28–6.92 (m) 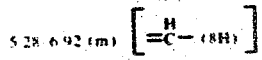

1,1-bis(1'-methyl-2'-vinyl-4',6'-heptadienoxy)butane

Figure 2:
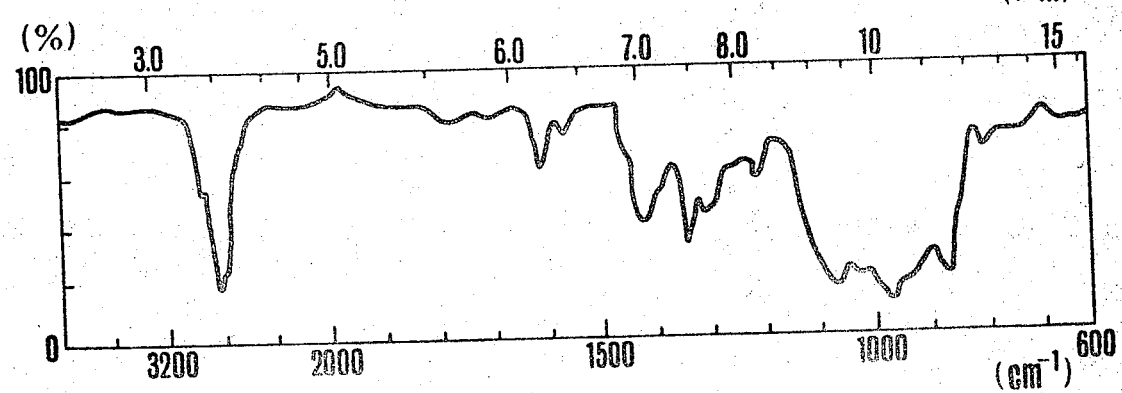
FIG. 2 represents an infrared absorption spectrum of 1,1-bis(1'-methyl-2'-vinyl-4',6'-heptadienoxy)butane.

Boiling point: More than 150° C/2mmHg (more than 320° C/760mmHg)
Ultraviolet absorption: λmax = 229 mμ
Infrared absorption spectrum: as shown in FIG. 2
Refractive Index: $n_D^{25}$ = 1.4846
Specific gravity: $d_4^{15}$ = 0.9025
Viscosity: η=22.1 cst (centistokes) (25° C)
Molecular weight: 365 (VPO method) (Theoretical value 358.5)
NMR: Measurement values obtained from CCl₄ solution and tetramethylsilane
δ(CCl₄) ppm 0.68–1.23 (m) [ —CH₃ (9H) ]

1.23–1.80 (m) [ —CH₂— (4H) ]

1.80–2.53 (m) 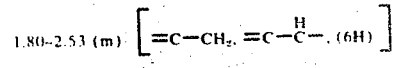

3.20–3.80 (m) 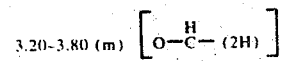

4.40–4.75 (m) 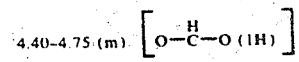

4.75–5.30 (m) [ =CH₂ (8H) ]

5.30–6.90 (m) 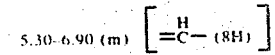

1,1-bis(1'-methyl-2'-vinyl-4',6'-heptadienoxy)octane

Figure 3:
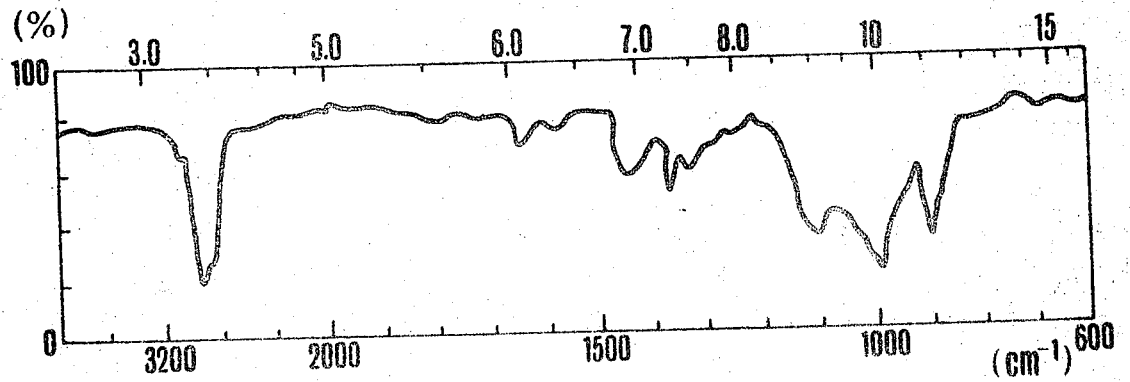
FIG. 3 represents an infrared absorption spectrum of 1,1-bis(1'-methyl-2'-vinyl-4',6'-heptadienoxy)octane.
Figure 1:
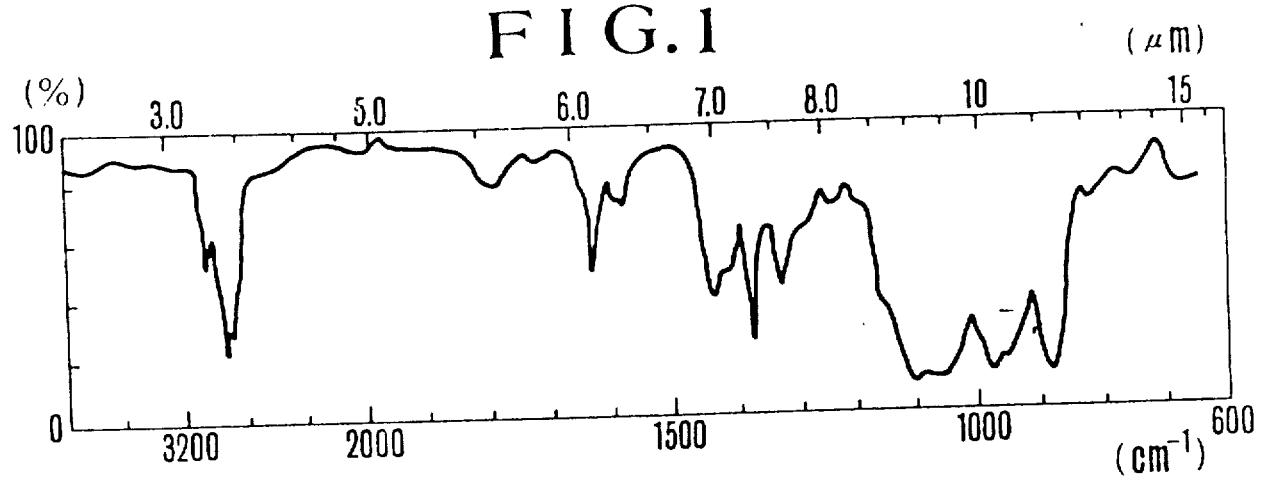
Figure 2:
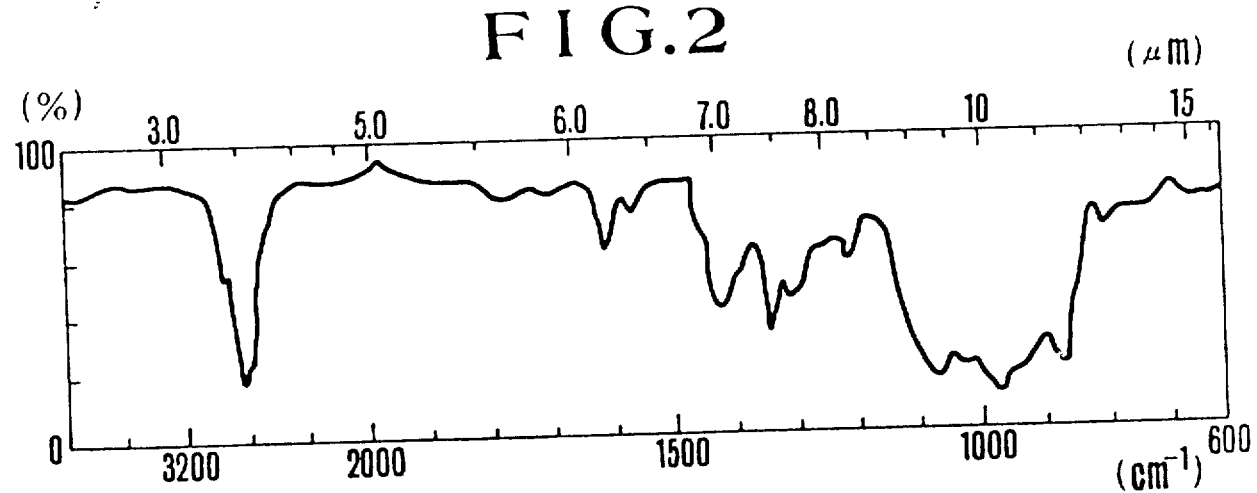
Figure 3:
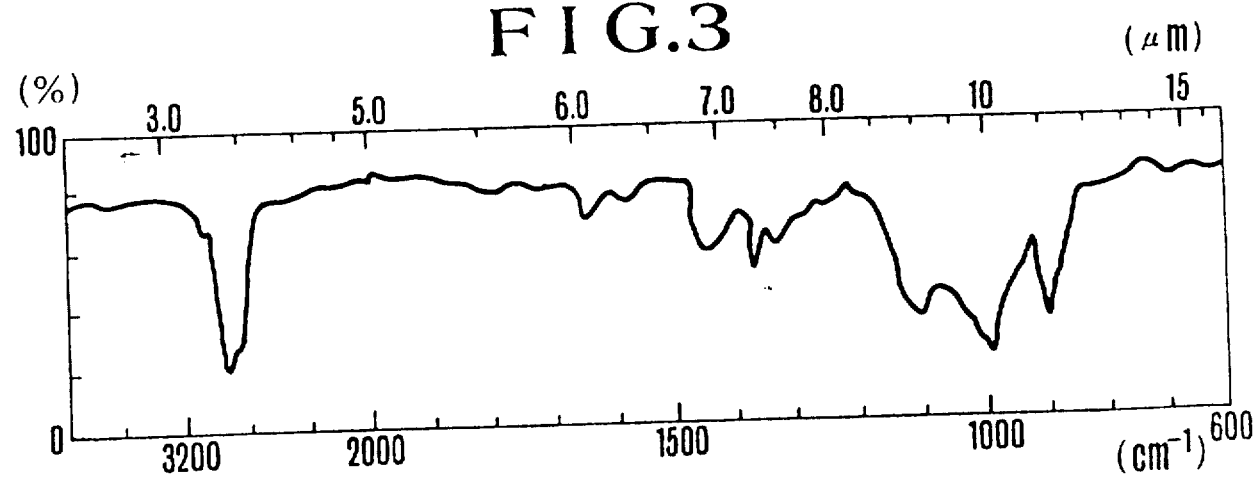

Boiling point: More than 150° C/2mmHg (more than 320° C/760mmHg)
Ultraviolet absorption: λmax = 229 mμ
Infrared absorption spectrum: as shown in FIG. 3
Refractive index: $n_D^{25}$ = 1.4834
Specific gravity: $d_4^{15}$ = 0.8884
Viscosity: η=19.2 cst (centistokes) (25° C)
Molecular weight: 413 (VPO method) (Theoretical value 414.5)
NMR: Measurement values obtained from CCl₄ solution and tetramethylsilane
δ(CCl₄)ppm 0.75–1.20 (m) [ —CH₃ (9H) ]

1.20–1.80 (m) [ —CH₂— (12H) ]

1.80–2.55 (m) 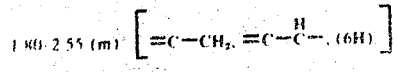

3.13–3.83 (m) 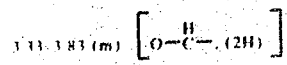

4.48–4.75 (m) 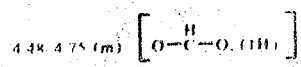

4.75–5.30 (m) [ =CH₂ (8H) ]

5.30–6.73 (m) 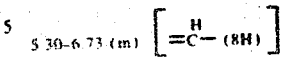

In each of the figures, the vertical axis represents percent transmission, the upper horizontal axis shows wave length (micron) and the lower horizontal axis indicates number of waves (cm⁻¹).

Since the compounds of the present invention have the backbone structure of 1-methyl-2-vinyl-4,6-heptadienol, they are quite reactive and are readily air cured by heat, light, radiation, electron rays and the like. This curing reaction may be effected by simultaneous use of an organic peroxide, azobis-isobutylonitrile or some other radical source. Further, the compounds of the present invention are oxidatively cross-linked and cured at room temperature either in the presence, or absence, of an oxidizing catalyst such as cobalt naphthenate. The compounds of this invention are also useful as synthetic drying oils and can be used advantageously as reactive diluents for cross-linking resins such as air-drying alkyd resins, 1,2-polybutadiene resin, diallylphthalate resins and unsaturated polyester resins. When a cross-linking resin paint is used for coating, a thinner or some other similar solvent is used to increase the workability of the paint. The solvent is necessary only at the time of coating and afterwards it evaporates from the paint film. Use of a volatile solvent of this type is undesirable considering the effects it has on air pollution, safety of workers and saving of resources. In contrast, when one of the compounds of this invention is used as the diluent, it offers the advantage that the paint can be applied without a solvent thereby enabling the coating to cure in its unaltered form. By using the compounds of this invention, the environmental pollution resulting from the use of a solvent in a coating operation is largely eliminated. Thus, the present invention not only contributes to the field of coating with alkyd resin paints, oil-based paints and water-based paints but also provides advantageous vehicles for adhesive agents, inks, etc. Moreover, the compounds of this invention have two conjugated double bonds and two vinyl substituents in the molecule. Therefore, they find utility in an extremely wide range of applications as intermediates for various chemicals.

The present invention will be illustrated but not limited by the following examples.

EXAMPLE 1

In a 100-ml three-necked flask fitted with an air-tight agitator, 20.4 g of 1-methyl-2-vinyl-4,6-heptadienol and 5 g of anhydrous calcium chloride, while cooled under an ice bath, were agitated until homogenized. Under continued agitation, 4.4 g of acetaldehyde was added and then 0.1 g of paratoluene sulfonic acid was added dropwise. The mixture was brought back to room temperature and agitated for 20 hours. At the end of the reaction period, the calcium chloride was removed by filtration and was washed with n-pentane. The washings were combined with the filtrate. The solution was neutralized with a 5% sodium carbonate solution and dried with sodium sulfate. n-Pentane, unreacted acetaldehyde and unreacted 1-methyl-2-vinyl-4,6-heptadienol were removed by distillation and the fraction distilling out at 144°–148° C/2 mmHg was collected. The fraction was identified to be 1,1-bis(1'-methyl-2'-vinyl-4',6'-heptadienoxy)ethane. The yield was 96%. The general properties of the substance were as indicated previously.

EXAMPLE 2

In a 500-ml three-necked flask fitted with an air-tight agitator, 152 g of 1-methyl-2-vinyl-4,6-heptadienol and 66.6 g of anhydrous calcium chloride were agitated until homogenized while cooled under an ice bath. 72 g of n-butylaldehyde was then added under continued agitation. The resultant mixture was brought to a temperature of 25° C and agitated for 22 hours. At the end of the reaction period, calcium chloride was separated by filtration and washed with n-pentane. The washings and the filtrate were combined and the solution was dried with sodium sulfate. The anhydrous mixture was distilled to remove n-pentane, unreacted butylaldehyde and unreacted 1-methyl-2-vinyl-4,6-heptadienol. The reaction product was isolated by a silica gel, chromatographic column. This product was identified to be 1,1-bis(1'-methyl-2'-vinyl-4',6'-heptadienoxy)butane. The yield was 95 with general properties as previously indicated.

EXAMPLE 3

In a 500-ml three-necked flask fitted with an air-tight agitator, 152 g of 1-methyl-2-vinyl-4,6-heptadienol and 66.6 g of anhydrous calcium chloride were agitated until homogenized while kept cooled under an ice bath. 128 g of n-octylaldehyde was then added. The resultant mixture was brought up to 25° C under continuous agitation and was so maintained for 4 hours to bring the reaction to completion. After the reaction mixture was treated by a procedure similar to that of Example 2 to remove unreacted reactants by distillation. The product was isolated by a chromatographic column of silica gel. This substance was identified to be 1,1-bis(1'-methyl-2'-vinyl-4',6'-heptadienoxy)octane. The yield was 90 percent. The general properties of this substance were as indicated previously.

What is claimed is:
1. A 1,1-bis(1'-methyl-2'-vinyl-4',6'-heptadienoxy)alkane of the generic formula:

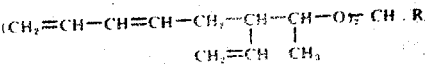

wherein R denotes H or an alkyl group of 1 to 7 carbon atoms.

2. The compound according to claim 1, wherein the 1,1-bis(1'-methyl-2'-vinyl-4',6'-heptadienoxy)alkane is 1,1-bis(1'-methyl-2'-vinyl-4',6'-heptadienoxy)ethane.

3. The compound according to claim 1, wherein the 1,1-bis(1'-methyl-2'-vinyl-4',6'-heptadienoxy)alkane is 1,1-bis(1'-methyl-2'-vinyl-4',6'-heptadienoxy)butane.

4. The compound according to claim 1, wherein the 1,1-bis(1'-methyl-2'-vinyl-4',6'-heptadienoxy)alkane is 1'1-bis(1'-methyl-2'-vinyl-4',6'-heptadienoxy)octane.

UNITED STATES PATENT OFFICE
CERTIFICATE OF CORRECTION

Patent No. 4,008,283                        Dated February 15, 1977

Inventor(s) Satoru Enomoto et al.

It is certified that error appears in the above-identified patent and that said Letters Patent are hereby corrected as shown below:

Insert the sheet of drawings as part of Letters Patent 4,008,283 per attachment.

On the cover sheet the illustrative figure should appear as figure one.

Signed and Sealed this

Fourteenth Day of June 1977

[SEAL]

Attest:

RUTH C. MASON
*Attesting Officer*

C. MARSHALL DANN
*Commissioner of Patents and Trademarks*